US009447108B2

(12) United States Patent
Fülöp et al.

(10) Patent No.: US 9,447,108 B2
(45) Date of Patent: Sep. 20, 2016

(54) DEUTERATED MORPHINE DERIVATIVES

(71) Applicant: SZEGEDI TUDOMÁNYEGYETEM, Szeged (HU)

(72) Inventors: Ferenc Fülöp, Szeged (HU); István Mándity, Szeged (HU)

(73) Assignee: Szegedi Tudományegyetem, Szeged (HU)

( * ) Notice: Subject to any disclaimer, the term of this patent is extended or adjusted under 35 U.S.C. 154(b) by 0 days.

(21) Appl. No.: 14/781,116

(22) PCT Filed: Apr. 14, 2014

(86) PCT No.: PCT/HU2014/000030
§ 371 (c)(1),
(2) Date: Sep. 29, 2015

(87) PCT Pub. No.: WO2014/170704
PCT Pub. Date: Oct. 23, 2014

(65) Prior Publication Data
US 2016/0052931 A1  Feb. 25, 2016

(30) Foreign Application Priority Data

Apr. 15, 2013 (HU) ..................................... 1300221

(51) Int. Cl.
*A61K 31/485* (2006.01)
*C07D 489/02* (2006.01)
*A61K 45/06* (2006.01)
*C07D 489/00* (2006.01)

(52) U.S. Cl.
CPC ........... *C07D 489/02* (2013.01); *A61K 31/485* (2013.01); *A61K 45/06* (2013.01); *C07D 489/00* (2013.01)

(58) Field of Classification Search
USPC ..................................... 514/282; 546/44, 45
See application file for complete search history.

(56) References Cited

U.S. PATENT DOCUMENTS 8,703,099 B2 * 4/2014 Reis ..................... C07D 243/24
424/9.1

OTHER PUBLICATIONS

Mutlib et al.: "The Species-Dependent Metabolism of Efavirenz Produces a Nephrotoxic Glutathione Conjugate in Rats", Toxicology and Applied Pharmacology, 2000, vol. 169, pp. 102-113.
Hahesy et al: "Temporal association between childhood psychopathology and substance use disorders: findings from a sample of adults with opioid or alcohol dependency", Psychiatry Research, 2002, vol. 109, pp. 245-253.
Corbett et al.: "75 years of opioid research: the exciting but vain quest for the Holy Grail", British Journal of Pharmacology, 2006, vol. 147, pp. S153 S162.
Hargreaves et al.: "A new and sensitive method for measuring thermal nociception in cutaneous hyperalgesia", Pain, 1988, vol. 32, pp. 77-88.
Benyhe et al.: "Met5-Enkephalin-Arg 6-Phe7, an Endogenous Neuropeptide, Binds to Multiple Opioid and Nonopioid Sites in Rat Brain", Journal of Neuroscience Research, 1997, vol. 48, pp. 249-258.
Elison et al.: "Effect of Deuteration of N—CH3 Group on Potency and Enzymatic N-Demethylation of Morphine", Science, 1961, vol. 134, No. 3485, pp. 1078-1079.
Gilbert et al.: "Pharmacological characterization of dihydromorphine, 6-acetyldihydromorphine and dihydroheroin analgesia and their differentiation from morphine", European Journal of Pharmacology, 2004, vol. 492, pp. 123-130.
Jelsma: "The Development of International Drug Control: Lessons Learned and Strategic Challenges for the Future", Global Commission on Drug Policies, 2011, pp. 1-16.
Schatman et al.: "A practical and ethical solution to the opioid scheduling conundrum", Journal of Pain Research, 2014, vol. 7, pp. 1-3.

* cited by examiner

*Primary Examiner* — Charanjit Aulakh
(74) *Attorney, Agent, or Firm* — Jason D. Voight

(57) ABSTRACT

The invention relates to new morphine derivatives deuterated at the 7,8-position of the morphine ring, furthermore to a process for the preparation thereof, and to pharmaceutical compositions comprising them. The new deuterated morphine derivatives show high and selective μ-opioid receptor binding activity leading to the benefit of higher analgesic activity at lower dosages inducing thereby reduced adverse effects compared to the hydrogenated derivatives. The compounds of the invention are useful for example in the treatment of pain or can be used as antitussive agents with a reduced risk of the possibility of drug abuse.

19 Claims, No Drawings

DEUTERATED MORPHINE DERIVATIVES

This is the national stage of International Application PCT/HU2014/000030, filed Apr. 14, 2014.

BACKGROUND OF THE INVENTION

1. Technical Field of the Invention

The invention relates to new deuterated morphine derivatives of general formula (I), and stereoisomers including enantiomers, diastereomers, racemic mixtures, mixtures of enantiomers or combinations thereof, as well as polymorphs, tautomers, solvates, salts, esters and prodrugs thereof, furthermore to a process for the preparation thereof, and to pharmaceutical compositions comprising them.

2. Description of the Prior Art

Morphine, member of the opiates, is the most commonly used narcotic analgesic agent for the treatment of severe chronic and acute pain. An example of chronic pain is the pain which occurs in cancer. An example of acute pain is the pain which may occur after operations. Morphine is a powerful analgesic routinely used to reduce pain in humans. For example, surgery patients are typically instructed to take 5 to 10 mg of morphine per person to alleviate pain caused by the surgical procedure. In some cases, patients suffering from extreme pain (e.g., burn victims or cancer patients) are instructed to take higher doses of morphine. For moderate to severe pain, the optimal intramuscular dosage is considered to be 10 mg per 70 kg body weight every four hours. The typical dose range is from 5 to 20 mg every four hours, depending on the severity of the pain. The oral dose range is between 8 and 20 mg, but orally administered morphine has substantially less analgesic potency. The intravenous route is used primarily for severe post-operative pain or in emergency. In such cases, the dose range is between 4 and 10 mg, and the analgesic effect ensues almost immediately (Hardman, J. G.; Limbird, L. E.; Molinoff, P. B.; Ruddon, R. W. Goodman Gilman, A. Goodman and Gilman's The Pharmacological Basis of Therapeutics, Ninth Edition, 1996).

Dihydromorphine is slightly stronger than morphine as an analgesic with a similar side effect profile. Dihydromorphine may have better bioavailability after oral administration than morphine. The onset of action is more rapid than that of morphine and it also tends to have a longer duration of action, generally 4-7 hours. At the present time, dihydromorphine is most commonly used in Japan, and various European and Asian countries. A United Nations report in 1993 stated increases in use of dihydromorphine in some Central European countries, and, later, WHO and EU reports show the same, although distinction is not made between use of dihydromorphine (Paramorfan) as an analgesic product, and the use of dihydromorphine in the manufacture of other drugs. The latter is also the case in the United States, where it is seen exclusively as an intermediate in the manufacture of dihydrocodeine as well as in some methods of manufacture of hydrocodone, hydromorphone, and related drugs (http://en.wikipedia.org/wiki/Dihdromorphine).

The opiates used up until now for treating pain are indeed highly effective but have a number of unpleasant and/or undesirable side effects, e.g. a short duration of activity, respiratory depression, nausea, constipation, diuresis and euphoria and they are also addictive. The property of opioids to induce euphoria is considered the basis for their potential to be abused. Moreover, the very effective and rapidly acting diacetyl derivative of morphine (heroin) cannot have any clinical applications because of abuse potential.

The ambivalent nature of said substances, i.e. their potential to offer medical benefit but also to promote abuse, have been known for a long time (Thesis of Dr. Jung S.; dgra.de/studiengang/pdf/master_jung_s.pdf and the references cited therein). As a consequence an international control system was established already at the beginning of the last century to prevent the abuse of these substances and to limit their licit use to purely medical and scientific purposes (Bayer I., Ghodse H.; "Evolution of International Drug Control, 1945-1995", Bulletin on Narcotics Volume LI, United Nation Office on Drugs and Crime, 1999).

Despite tight international control, diversion and abuse of psychoactive substances still constitute major public health and social problems in the majority of countries worldwide. Interestingly, in the U.S., which is the world's largest single market for illicit drugs (2004 INCB report: E/INCB/2004/1), abuse of prescription medicines, especially of those containing morphine, oxycodone, hydrocodone, codeine and other opioids, has become a major problem.

According to the U.S. National institute of Drug Abuse (NIDA, InfoFacts 2005), opioid abuse and dependence may contribute to other serious health problems including the spread of HIV or hepatitis (because of risky behavior like needle sharing and unsafe sex), adverse cardiovascular effects, ranging from abnormal heart rate to heart attacks, liver damage. Opioid abuse may also be associated with psychiatric illness such as depression and generalized anxiety disorder [Hahesy et al; "Temporal association between childhood psychopathy and substance use disorders: Findings from a sample of adults with alcohol or opioid dependency", *Psychiatry Res.* 109(3): 245-253. 2002], and cognitive impairment (Ornstein et al.; "Profiles of cognitive dysfunction in chronic amphetamine and heroin abusers", *Neuropsychopharmacology*, 23; 113-126, 2000). In addition to these adverse medical consequences, opioid abuse and dependence is also known to contribute to severe social problems such as individual, family and community disintegration.

While it is important to make efficacious medicines containing psychoactive substances available to patients who need them, it is at the same time imperative to judge their potential for abuse, i.e. their "abuse liability" and, if necessary, take special precautions to prevent abuse and diversion of these products. A sensible balance between access to useful drugs and protecting the public from the consequences and dangers of ready access to substances of abuse must be found (Thesis of Dr. Jung, S.; dgra.de/studiengang/pdf/master_jung_s.pdf and the references cited therein). Moreover, there is a big need for novel and more potent opioid derivatives. (Corbett, A. D.; Henderson, G. McKnight, A. T.; Paterson, S. J.; *Brit. J. Pharm.* 147, S153-S162, 2006.) For decades long only one novel opioid derivative, the tapentadol has been introduced to therapeutic use. (Hartrick, C.; van Hove, I.; Stegmann, J. U.; Oh, C.; Upmalis, D.; *Clinical Therapeutics* 31, 260-271, 2009.)

In the U.S. alone, approximately 100 million people suffer from acute and chronic pain. Because of this potentially large market, pharmaceutical industry is in continuous search for new substances to treat neurological and psychiatric disorders.

During the last 2 decades, there has been a dramatic increase in the use of strong opioids for chronic non-cancer pain. This increase has been accompanied by a steep increase in abuse, misuse, and both fatal and non-fatal overdoses involving prescription opioids. The situation is already alarming in the US. Prescription opioid-related harm is a complex, multifactorial issue that requires a multifaceted solution. In this respect, formulations of opioid analgesics designed to resist or deter abuse may be a useful component of a comprehensive opioid risk minimization program. Such formulations have or are being developed.

Abuse-resistant opioids include those that use some kind of physical barrier to prevent tampering with the formulation. For example the patent application EP 1986650 A1 discloses special dosage forms used for the prevention of the illicit use of opioid agonist formulations. Moreover, it has been stated that drug formulations present significant barriers to tampering reduce, but do not totally eliminate misuse (Cone, E. J.; *Drug Alc.l Dep., S*31-S39, 2006).

Abuse-deterrent opioids are not necessarily resistant to tampering, but contain substances that are designed to make the formulation less attractive to abusers. Two products intended to deter abuse were reviewed by the US Food and Drug Administration (FDA) (Bannwarth, B. *Drugs,* 72, 1713-1723, 2012).

The first composition (Embeda®) consists of morphine for extended-release with sequestered naltrexone, an opioid antagonist that is released if the tablet is compromised by chewing or crushing. Although Embeda® exhibited abuse-deterrent features, its label warns that it can be abused in a manner similar to other opioid agonists. Furthermore, tampering with Embeda® will result in the release of naltrexone, which may precipitate withdrawal in opioid-tolerant individuals. In March 2011, all dosage forms of Embeda® were recalled because the product failed to meet routine stability standards, and its return date to the market is currently unknown (http://www.reuters.com/article/2011/03/16/us-pfizer-recallidUSTRE72FA3Q20110316).

The second product (Acurox®) was intended to be both tamper resistant and abuse deterrent. It consisted of an immediate-release oxycodone tablet with subtherapeutic niacin as an aversive agent and used a gel-forming ingredient designed to inhibit inhalation and prevent extraction of the drug for injection. The new drug application for Acurox® was rejected in 2010 by the FDA because of concerns about the potential abuse-deterrent benefits of niacin (Mastropietro D J, Omidian H, *Drug Dev. Ind. Pharm.* Epub 2012 Apr. 26).

While acknowledging that no formulation can be expected to deter all types of opioid-abusive behaviors and no product is likely to be abuse proof in the hands of clear and determined abusers, for the reductions in abuse new products would provide an incremental step towards safer prescription of opioids (*Drugs,* 72, 1713-1723. 2012). Consequently, there is a continuous need for safe and efficacious drugs.

Thus, the principal aim of the present invention is the provision of compounds with higher receptor binding affinity resulting in improved pharmacological properties for example in higher analgesic and antitussive activity, with longer duration of action and reduced adverse effects through the administration of lower doses, and additionally with a reduced risk of the possibility of drug abuse.

The present invention provides novel deuterated morphine derivatives of general formula (I) with high and selective μ-opioid receptor activity. It has been surprisingly and unexpectedly found that morphine derivatives deuterated in 7,8-position of the morphine ring show high opioid receptor binding activity which is selective towards the μ-receptor whereby they are useful for example in the management of pain or may be used as antitussive drugs. The analgesic effect of compounds of invention is higher and of prolonged duration when compared to that of the corresponding hydrogenated derivatives, thus permitting the administration of lower dosages, resulting in reduced adverse effects. Moreover because of the incorporated deuterium atoms in the morphine ring itself in positions not attained by the first steps of the metabolic pathway the presence of the compounds or that of their metabolites can be followed up easily in a patient leading to higher safety in application and drug abuse cases may be discovered and prevented.

The deuterium is a naturally occurring, stable, non-radioactive hydrogen isotope. The hydrogen atom contains one electron, and one proton in the nucleus. Consequently the mass of the hydrogen atom is one AMU. The deuterium atom contains one electron and one proton and one neutron in the nucleus. Consequently the mass of the deuterium atom is two AMU. Natural occurrence of deuterium atom comparing to the hydrogen atom is 1:6600 (Marter, W. L.; Hayes, D. W.; Jones, D. W. *Encyclopedia of Chemical Processing and Design,* Issue 15, McKetta, J. C.; Cunningham, W. A. Eds, Marcel Dekker, 1982.). The toxicity of deuterium is very low. The human body tolerates very high heavy water content, for example a body fluid with a deuterium content of 15-23% showed no harmful effect (Blagojevic, N.; Storr, G.; Allen, J. B.; *Advanced Medical Publishing,* Madison Wis., 1994).

Comparing a deuterium containing molecule with the corresponding unlabeled one, many properties (such as: molecule shape, surface, etc.) of both are identical, due to the same electron cloud around the molecules, the incorporation of deuterium atom does not influence the molecular shape. For example the perdeuterated variant of arginaze-I enzyme showed the same behavior in biological assays and X-ray investigation compared to the native hydrogenated one (Di Costanzo, L.; Moulin, M.; Haertlein, M.; Meilleur, F.; Christianson, D. W.; *Arch. Biochem. Biophys,* 465, 82, 2007).

However, the physical properties of deuterated derivatives may be different from that of the hydrogen containing ones. Due to the change of hydrogen for deuterium the hydrophobicity of the molecule can decrease or if the deuteration place is next to an ionizable functional group, the $pK_a$ can alter as well. Consequently, the receptor binding selectivity or affinity of a deuterated drug molecule may change compared to the hydrogen containing one. One possible explanation of this effect is that the C-D bond is 6-10 times stronger, than the C—H bond. Accordingly the C-D bond is less polarizable, cleavable and reactive. This phenomenon is called kinetic isotope effect (KIE) (Bell R. P.; *Chem. Soc. Rev.* 3, 513, 1974). Consequently the KIE can influence the binding of drug molecules to their receptor or can alter the metabolism of deuterium labeled drugs if the deuteration point is next to the metabolization place.

On the other hand in real biological systems, many rival processes may alter the action of KIE (Fisher, M. B.; Henne, K. R.; Boer; J. *Curr. Opin. Drug. Discov. Devel.* 9, 110, 2006). There are three ways for said alteration: (i) slower metabolization (Kushner, D. J.; Baker, A.; Dunstall, T. G.; *Can. J Physiol. Pharmacol.,* 77, 79, 1999); (ii) appearance of alternative metabolizing ways (Kushner, D. J.; Baker, A.; Dunstall, T. G.; *Can. J Physiol. Pharmacol.* 77, 79, 1999, and Mutlib, A. E.; Gerson, R. J.; Meunier, P. C.; *Toxicol. Appl. Pharmacol.,* 169, 102, 2000) and (iii) and in some rare cases, the metabolism can be accelerated as well (only one in vitro experiment) (http://www.concertpharma.com/about/documents/IPT32ConcertPharma.pdf).

Slower metabolism can appear in two different forms as well. In the case of slower metabolism in the systemic blood stream the half-life of the molecule will be increased, leading to a broader AUC curve, consequently the duration of the effect, i.e. the time interval between two dosages, will be longer. The slower metabolism in the liver or in the intestinal wall (before the systemic blood stream) will lead to higher $c_{max}$ values. Consequently lower dosages can be applied.

In the case of alternative metabolizing ways, new active metabolites may appear. This phenomenon can result in a protracted effect and shorter time intervals between two dosages (Mutlib, A. E.; Gerson, R. J.; Meunier, P. C.; Toxicol. Appl. Pharmacol. 169, 102, 2000).

Deuterium containing samples have been widely used as internal standards in pharmacokinetic investigation, but there are only few examples of studying the pharmacodynamics of deuterated drug molecules. Deuteration usually changes one or more pharmacodynamic properties of the compound, for example absorption, distribution, metabolism and excretion properties. For example amphetamines are more readily transported into the brain in deuterated form (Wenzel, M., Erhöhte Gehirn-affinität von 131J-markierten N-(Alkyl)-amphetaminen nach Deuterierung. J. Labelled Compd. Radiopharm., 27: 1143-1155, 1989); halogenated anaesthetics, such as selvoflurane, when deuterated are no longer oxidized to toxic forms within the body (Baker M T, Ronnenberg, Jr. W C, Ruzicka J A, Chiang C-K, Tinker J H.; Inhibitory effects of deuterium substitution on the metabolism of sevoflurane by the rat. Drug Metabolism and Disposition 21: 1170-1171. 1993). The metabolism of the deuterated fludalanin occurred in an alternative way (Kahan, F.; Chem. Engin. News., 87, 2009), but in some patients with metabolic disorders the benefit of the altered metabolism could not be exploited. Harmful drug interactions caused by a paroxetin metabolite may perhaps be avoided by a deuterated paroxetin derivative (CTP-347) metabolizing in a different way (http://www.concertpharma.com/).

A deuterated morphinan compound bearing deuterated substituent in the side chains of the morphine ring i.e. N-$d_3$-methyl-3-$d_3$-methoxy-mophinan, is reported in the patent application EP 2152709 A1 to demonstrate a longer clearance and produce a higher plasma exposure level hours post-dosing as compared to their non-deuterated form. Since the N- and O-demethylated metabolites of the morphinan formed via multiple catalytic steps are responsible for its biological action an altered metabolic pathway due to said deuterated derivative lead to the beneficial effect in this case.

SUMMARY OF THE INVENTION

The invention is directed to new deuterated morphine derivatives which show broad utility by exhibiting high and selective μ-opioid receptor activity whereby are useful for example in the treatment of pain or can be used as antitussive agents with a reduced risk of the possibility of drug abuse.

The invention is based upon the unexpected finding that the novel morphine derivatives of general formula (I) deuterated at the 7,8-position of the morphine ring show high and selective μ-opioid receptor binding activity leading to the benefit of higher analgesic activity at lower dosages inducing thereby reduced adverse effects compared to the hydrogenated derivatives. Moreover because of the incorporated deuterium atoms in the morphine ring itself in positions not attained by the first steps of the metabolic pathway the presence of the compounds or that of their metabolites can be followed up easily in a patient leading to higher safety in application and drug abuse cases may be discovered and prevented.

DETAILED DESCRIPTION OF THE INVENTION

In one aspect the present invention provides novel deuterated morphine derivatives of general formula (I),

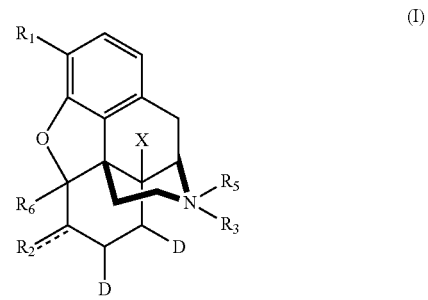

wherein
$R_1$ is —OH, —OR$_4$, —O-2,4-dinitrophenyl, —OC(=O) C$_{1-6}$alkyl, —OC(=O)phenyl, —OC(=O)pyridyl;
$R_2$ is hydrogen, —OH, —OR$_4$, —Cl, —N$_3$, bis(2-chloroethyl)amino-, —OC(=O)—C$_{1-16}$alkyl, —OC(=O)phenyl, —OC(=O)pyridyl, —(N-methyl-N—C(=O)—CH=CH-fur-3-yl), and the dotted line is absent or
$R_2$ is —O, —CH$_2$, —N—NH$_2$, —NOH, —N—O—C$_{1-6}$alkyl wherein the alkyl is optionally substituted with a caboxyl group, and the dotted line represents a chemical bond,
$R_3$ is hydrogen, —O, —C$_{1-6}$ alkyl optionally substituted by phenyl, (C$_{3-7}$ cycloalkyl)-(C$_{1-6}$ alkyl)-, (C$_{1-6}$alkyl)—O—(C$_{1-6}$alkyl), —C$_{2-7}$ alkenyl;
$R_4$ is —C$_{1-6}$ alkyl optionally substituted by a phenyl or by a 6 membered saturated heterocycle attached by a nitrogen and containing at least one more heteroatom selected from O, S and N;
$R_5$ is absent or is —C$_{1-6}$ alkyl and the ring nitrogen bears a positive charge;
$R_6$ is hydrogen, —C$_{1-6}$ alkyl;
X is hydrogen, —OH, —OR$_4$, —O-cinnamoyl, —NH(C$_{1-6}$ alkyl);
D is deuterium
and stereoisomers including enantiomers, diastereomers, racemic mixtures, mixtures of enantiomers or combinations thereof, as well as polymorphs, tautomers, solvates, salts, esters and prodrugs thereof.

The compounds depicted with the general formula I and stereoisomers including enantiomers, diastereomers, racemic mixtures, mixtures of enantiomers or combinations thereof, as well as polymorphs, tautomers, solvates, salts, esters and prodrugs thereof are useful for example in the management of pain, dyspnea, are useful as antitussive agents, as constipants, anti-dependence agents, furthermore are useful in the management of premature labor contractions, brain injury, cardiovascular diseases, chronic pain, intractable pain, polytraumatization, acute myocardial infarction, shock, potentiation of narcosis, cardial dyspnoe, lung edema, biliary and renal grapes, arthritis, chronic pain of joints, chronic inflammatory pain, neuropathic pain, sympathetically mediated pain, pain associated with gastrointestinal dysfunction, intractable coughing, painful eye conditions, dermatitis, addiction disorders, fatigue caused by cancer, pain of terminal illness, cancer pain, burn pain, headache, obstetrical analgesia, cough as antitussive agents, dyspnea in some special cases, diarrhea, certain surgical anesthesia, maintenance drug for opioid dependent peoples, treatment of opioid overdosage, acute pain, muscle pain, bone pain, post-operative pain, migraine, lumbar pain, arthrosis pain, pain associated with diabetes, pain associated with AIDS, some cases of productive chest cough, non-productive cough, flue, dry cough, chronic coughing, barking cough, whooping cough, psychogenic cough, reflex cough and the like.

In a further aspect the invention provides preferred compounds of formula (I) wherein $R_1$ is —OH, —O-methyl, —O-ethyl-, —O-benzyl, —O-(2, 4-dinitro)phenyl, —O-acetyl, —O-propionyl, —O-benzoyl, —O—(C=O)nicotinyl, —O-(2-morpholino)-ethyl;

$R_2$ is —H, —OH, —Cl, bis(2-chloroethyl)amino-, —O-methyl, —O-propionyl, —O-acetyl, —O-benzoyl, —O—(C=O)nicotinyl, —O—(C=O)myristyl, —(N-methyl-N—C(=O)—CH=CH-fur-3-yl) and the dotted line is absent, or $R_2$ is —CH$_2$, —O, —N—O—CH$_2$COOH, —N—NH$_2$, and the dotted line represents a chemical bond;

$R_3$ is —H, —O, -methyl, cyclopropylmethyl-, phenylethyl-, -pentyl, methoxyethyl-, cyclobutylmethyl-, -allyl;

$R_4$ is —H, -methyl, -ethyl, benzyl;

$R_5$ is -methyl and the ring nitrogen bears a positive charge;

$R_6$ is —H, -methyl;

X is hydrogen, —OH, —O-cinnamoyl, —NHpentyl, —O-methyl, —O-ethyl, —O—(CH$_2$)$_3$-Ph;

D is deuterium and stereoisomers including enantiomers, diastereomers, racemic mixtures, mixtures of enantiomers or combinations thereof, as well as polymorphs, tautomers, solvates, salts, esters and prodrugs thereof.

More preferred compounds of the invention are:

(5α,6α,7β8β)-3,6-dihydroxy-4,5-epoxy-17-methyl-(7,8-$^2$H$_2$)-morphinan (5α,6α,7β,8β)-4,5-epoxy-6-hydroxy-3-methoxy-17-methyl-(7,8-$^2$H$_2$)-morphinan (5α,6α,7β,8β)-4,5-epoxy-3-ethoxy-6-hydroxy-17-methyl-(7,8-$^2$H$_2$)-morphinan (5α,6α,7β,8β)-3,6-diacetoxy-4,5-epoxy-17-methyl-(7,8-$^2$H$_2$)-morphinan (5α,7β, 8β,14β)-4,5-epoxy-14-hydroxy-3-methoxy-17-methyl-(7,8-$^2$H$_2$)-morphinan-6-one and stereoisomers, enantiomers, diastereomers, racemic mixtures, mixtures of enantiomers or combinations thereof, as well as polymorphs, tautomers, solvates, salts, esters and prodrugs thereof.

Further aspects of the invention provide a pharmaceutical composition comprising a compound of general formula (I) or stereoisomers including, enantiomers, diastereomers, racemic mixtures, mixtures of enantiomers or combinations thereof, as well as polymorphs, tautomers, solvates, salts, esters and prodrugs thereof and one or more pharmaceutically acceptable carriers and/or excipients.

In a further aspect the invention provide preferred pharmaceutical compositions in the form of capsules, sachets, tablets, powders, granules, drops, syrups, suspensions, emulsions, oral therapeutic systems, soft gelatin capsules, lozenges, bolus, fine granule, powder, couplet, pill, dry syrup, coated preparations including sugarcoated tablets, couplets, film-coated tablets and coated granulated powder, elixir, limonade, extract, drinkable preparation and soft and hard capsule agents filling liquid or semi-solid substance, multi-layer granules, multi-layer tablets or dry coated tablet, tablets by separating granules, microcapsules, foaming pharmaceutical preparation, chewable preparation, dissolving preparation in the mouth, matrix preparation, solid solutions, lozenges, suppositories, rectal solutions, ready-to-use injectable solution, sterile injectable aqueous or oleaginous suspension, sterile powders, granules, tablets, suppositories, adhesive therapeutic systems, nasal aerosol or inhalation system, ointment, cream, enema formulation, iontophoretic application, coating an implantable medical device.

Further aspects of the invention provide a pharmaceutical composition comprising a compound of general formula (I) or stereoisomers including enantiomers, diastereomers, racemic mixtures, mixtures of enantiomers or combinations thereof, as well as polymorphs, tautomers, solvates, salts, esters and prodrugs thereof in a combination with one or more active agents.

In a further aspect the invention provide preferred pharmaceutical compositions comprising the compound of general formula (I) or stereoisomers including enantiomers, diastereomers, racemic mixtures, mixtures of enantiomers or combinations thereof, as well as polymorphs, tautomers, solvates, salts, esters and prodrugs thereof in a combination with one or more active agents selected from the group consisting of antihistamines, calcium channel blockers, sedatives, antiepileptics, anticonvulsant, other opioid agonists and antagonists, NMDA receptor antagonist, benzodiazepines, antiaddictives, phenotiazines, antidepressants, non-steroidal anti-inflammatory drugs, local anesthetics, psychostimulants, psychedelics, anticoagulants, glucocorticoids, muscle relaxants, parasympathomimetics, antiemetics, imidazoline receptor agonist, sympathomimetics, α$_2$-adrenergic receptor agonists, GABA receptor agonists, 5-HT1A agonist, proton pump inhibitors, histamine-2 receptor antagonist, intravenous anesthetics, cannabinoids, antibiotics, inhalational anaesthetics, antihypertensives, centrally acting non-opioid analgesics, stimulants, norepinephrine reuptake inhibitors, estrogen receptor agonists, antipsychotics, TNF inhibitors, expectorants, serotonin-norepinephrine reuptake inhibitors, serotonine receptor antagonists, antitumor agents, nasal decongestants, antihistamines, vitamines.

In another preferred aspect of the invention the additional active agents of the pharmaceutical composition are selected from the group consisting of cyclizine, naltrexone, ethorphine, paracetamol, metamizol sodium, coffein, ephedrine, naloxone, acetylsalicylic acid, ibuprofen, phenacetin, naproxen, indomethacin, diclofenac, promethazine, scopolamine, d,l-methylephedrine, chlorpheniramine, phenyltoloxamine citrate, lyzozime, romifidine, gabapentin, oxycodone, tramadol, ketamine, midazolam, mitragynine, ibogaine, pregabalin, escitalopram, citalopram, pentazocine, nalbuphine, dezocine, butorphanol, buprenorphine, ketorolac, ziconotide, cocaine, heparin, fentanyl, sufentanil, alfentanyl, remifentanil, dextromethorphan, bupivacaine, meperidine, tizanidine, alprazolam, neostigmine, norketamine, droperidol, clonidine, baclofen, lorazepam, nortriptyline, noradrenaline, carbachol, maprotiline, dexmedetomidine, omeprazole, phencyclidine, propofol, Δ$^9$-tetrahydrocannabinol, butamben, lidocaine, nifedipine, prednisone, amitriptyline, chlordiazepoxide, cefazolin, desipramine, serotonin, hydroxyzine, clonazepam, amphetamine, alcohol, acetaminophen, dipyrone, LSD, levomepromazine, diphenhydramine, minocycline, nitrous oxide, methadone, zolpidem, ethylketazocine, lisinopril, captopril, losartan, MDMA, flupirtin, caffeine, methoxetamine, phenobarbital, amfonelic acid, nisoxetine, tamoxifen, cyclazocine, chlorpromazine, cetirizine, ranitidine, trazodone, haloperidol, bupropion, prednisone, etanercept, levobupivacaine, ropivacaine, butalbital, guaifenesin, duloxetine, ondansetron, angiostatin K1-3, DL-α-difluoromethyl-omithine, endostatin, fumagillin, genistein, minocycline, staurosporine, (±)-thalidomide, bleomycim, carboplatin, carmustine, chlorambucil, cyclophosphamide, cis-diammineplatinum(II) dichloride (cisplatin), melphalan, mitoxantrone, oxaliplatin (±)-amethopterin (methotrexate), 3-amino-1,2,4-benzotriazine-1,4-dioxide, aminopterin, cytosine β-D-arabinofuranoside, 5-fluoro-5'-deoxyuridine, 5-fluorouracil, ganciclovir, hydroxyurea, mitomycin C, actinomycin D, daunorubicin, doxorubicin, homoharringtonine, idarubicin, S(+)-camptothecin, curcumin, (−)-deguelin, etoposide, formestane, fostriecin, hispidin, 2-imino-1-imidazoli-dineacetic acid (cyclocreatine), mevinolin, trichostatin A, tyrphostin AG 34, tyrphostin AG 879, 5-aza-2'-deoxycytidine, 5-azacytidine, cholecalciferol (Vitamin D3), hydroxytamoxifen, melatonin, mifepristone, raloxifene, all trans-retinal (Vitamin A aldehyde), retinoic acid, all trans (Vitamin A acid), 9-cis-retinoic Acid, 13-cis-retinoic acid, retinol (Vitamin A), tamoxifen, troglitazone, colchicine, dolastatin 15, nocodazole, paclitaxel, podophyllotoxin, rhizoxin, vinblastine, vincristine, vindesine, vinorelbine (Navelbine), 17-(allylamino)-17-demethoxygeldanamycin, 4-amino-1,8-naphthalimide, apigenin, brefeldin A, cimctidine, dichloromethylene-diphosphonic acid, leuprolide (Leuprorelin), luteinizing hormone-releasing hormone, pifithrin-α, rapamycin, sex hormone-binding globulin, thapsigargin, urinary trypsin inhibitor fragment (Bikunin), levo-methamphetamine, naphazoline, oxymetazoline, phenylephrine, phenylpropanolamine, propylhexedrine, synephrine, tetrahydrozoline, azelastine, carbinoxamine, levocetirizine, fexofenadine, diphenhydramine, brompheniramine, loratadine, clemastine, certirizine, Vitamin A (retinol), Vitamin B1 (thiamine), Vitamin B2 (riboflavin), Vitamin B3 (niacin), Vitamin B5 (pantothenic acid), Vitamin B6 (pyridoxine), Vitamin B7 (biotin), Vitamin B9 (folate), Vitamin B12 (cobalamin), Vitamin C (ascorbic acid), Vitamin D (calciferol), Vitamin E, Vitamin K, alloclamide, chloperastine, tipepidine, sodium dibunate, tipepidine, cloperastine fendizoate, codeine, dihydrocodeine, pentoxyverine, noscapine, carbetapentane, dimemorfan, benproperine, isoaminile, oxeladin, eprazinone, clobutinol, clofedanol, fominoben, I-methylephedrine, trimetoquinol, pseudoephedrine, phenylpropanolamine, methoxyphenamine, ambroxol, bromhexine, isopropamide and salts thereof.

In the most preferred aspect of the invention the additional active agents of the pharmaceutical composition are selected from the group consisting of cyclizine, naltrexone, buprenorphine, ethorphine, paracetamol, metamizol sodium, coffein, ephedrine, naloxone, acetylsalicylic acid, ibuprofen, phenacetin, naproxen, indomethacin, diclofenac, promethazine, scopolamine, d,l-methylephedrine, chlorpheniramine, phenyltoloxamine and lyzozime and salts thereof.

In a further aspect of the invention the pharmaceutical composition comprising an additional active agent said additional active agent is administered to a patient simultaneously, separately or sequentially with a compound of the general formula (I).

In a further aspect of the invention provides a process for the preparation of compounds of general formula (I) by reacting a 7,8-didehydro-morphine derivative of general formula (II)

(II)

wherein $R_1$, $R_2$, $R_3$, $R_4$, $R_5$, $R_6$ and X are the same as defined for formula (I), with deuterium gas in the presence of a catalyst or with organic and inorganic deuteride ion or deuterium radical or deuterium gas sources.

In a preferred aspect of the invention the preparation process proceeds in a reactor at elevated pressure, typically between 2-500 bars, with deuterium gas in the presence of Pd/BaSO$_4$ catalyst at a temperature range of 20-100° C. in an aprotic solvent.

Abbreviations

ANOVA: ANalysis Of Variances
AUC: area under curve
BRC: Biological Research Center, Szeged, Hungary
DAMGO: (2S)-2-[[2-[[(2R)-2-[[(2S)-2-amino-3-(4-hydroxyphenyl)propanoyl]amino]propanoyl]amino]acetyl]-methylamino]-N-(2-hydroxyethyl)-3-phenylpropanamide
FDA: Food and Drug Administration
Fisher-LSD test: Fisher's Least Significant Difference test
GABA: γ-aminobutyric acid
5-HT1A: Serotonin 1A receptor
KIE: kinetic isotope effect
LSD: Lysergic acid diethylamide
MDMA: 3,4-methylenedioxy-N-methamphetamine
MTD: maximum tolerated dose
NMR: Nuclear Magnetic Resonance
NMDA: N-methyl-D-aspartic acid
PWD: paw-withdrawal test
SEM: standard error of the mean
TNF: Tumor necrosis factors Definitions The term "pharmaceutically acceptable salts" in these instances refers to the relatively non-toxic, inorganic and organic acid or base addition salts of compounds of the present invention A "pharmaceutically acceptable salt" may be prepared from any compound of the invention having functionality capable of forming salts, for example a base functionality. Pharmaceutically acceptable salts may be prepared with organic or inorganic acids. Compounds of the invention that contain one or more basic functional groups are capable of forming pharmaceutically acceptable salts with pharmaceutically acceptable organic and inorganic acids. These salts can be prepared in situ during the final isolation and purification of the compounds of the invention, or by separately reacting a purified compound of the invention in its free base form with a suitable organic or inorganic acid, and isolating the salt thus formed. Examples of pharmaceutically acceptable salts include but are not limited to sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, tartrate, methanesulfonate, propanesulfonate, naphthalene-1-sulfonate, naphthalene-2-sulfonate, mandelate, adipate, alginate, mucate, aspartate, benzenesulfonate, butyrate, camphorate, camphorsulfonate, cyclopentanepropionate, digluconate, dodecylsulfate, ethanesulfonate, glucoheptanoate, glycerophosphate, hemisulfate, hexanoate, hydrochloride, hydrobromide, hydroiodide, 2-hydroxyethanesulfonate, 2-napthalenesulfonate, nicotinate, nitrate, palmoate, pectinate, persulfate, picrate, pivalate, salicylate, thiocyanate, tosylate, arginate and undecanoate. See, for example, Berge et al. "Pharmaceutical Salts", J. Pharm. Sci. 66:1-19 (1977) and the like. In one embodiment, pharmaceutically acceptable acid addition salts include those formed with mineral acids such as hydrochloric acid and hydrobromic acid, and especially those formed with organic acids such as maleic acid.

Acids commonly employed to form pharmaceutically acceptable salts include but are not limited to inorganic acids such as hydrogen bisulfide, hydrochloric acid, hydrobromic acid, hydroiodic acid, sulfuric acid and phosphoric acid, as well as organic acids such as paratoluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid.

Other acids, such as oxalic, while not in themselves pharmaceutically acceptable, may be employed in the preparation of salts useful as intermediates in obtaining the compounds of the invention and their pharmaceutically acceptable acid addition salts.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The N-oxides can be used as pharmaceutically acceptable alternatives as well.

The compounds of the invention containing one or more chiral centers may exist in enantiomeric and diastereomeric forms. The scope of the invention is intended to cover all isomers per se, as well as mixtures of cis and trans or α and β isomers, mixtures of diastereoisomers and racemic or non-racemic mixtures of enantiomers (optical isomers) as well.

It is possible using well known techniques to separate the various forms, and some embodiments of the invention may feature purified or enriched species of a given isomer.

The term deuterated as used herein refers to compound, where a double bond is saturated with deuterium containing reagents and the deuterium incorporation is more than 95%.

The term "alkyl" as used herein refers to a straight-chain, or branched chain saturated hydrocarbon radical having from one to sixteen carbons. Examples of alkyl radicals include methyl, ethyl, n-propyl, isopropyl, n-butyl, isobutyl, sec-butyl, tert-butyl, tert-amyl, pentyl, hexyl, heptyl, myristyl and the like.

The term "alkenyl" as used herein refers to a straight-chain, or branched chain hydrocarbon radical having one or two double bonds and from two to seven carbons. Examples of alkenyl radicals include allyl, vinyl and the like.

The term "cycloalkyl" as used herein refers to cyclic alkyl monoradicals wherein each cyclic moiety has from three to seven carbon atoms. Examples of cycloalkyl radicals include cyclopropyl, cyclobutyl, cyclopentyl, cyclohexyl and the like.

The term "alkoxy" as used herein refers to an alkyl-O— group wherein the term alkyl is defined as above. Examples of alkoxy groups include methoxy, ethoxy, n-propoxy, iso-propoxy, n-butoxy, iso-butoxy, sec-butoxy, tert-butoxy and the like.

The term "alkyl-O-alkyl" as used herein refers to an alkoxyalkyl group wherein the terms alkoxy and alkyl are defined as above. Examples of alkoxyalkyl group include methoxymethyl, etoxymethyl, methoxyethyl and the like.

The term "cycloalkyl-alkyl" as used herein refers to a straight-chain, or branched chain saturated hydrocarbon radical having from one to six carbons and substituted by a cyclic alkyl monoradical wherein the cyclic moiety has from three to seven carbon atoms. Examples of cycloalkyl-alkyl radicals include cyclopropyl-methyl, cyclobutyl-methyl and the like.

The term "saturated heterocycle" as used herein refers to a six membered saturated heterocycle attached by a nitrogen and having at least one more heteroatom like oxygen, sulfur, nitrogen. Examples of saturated heterocycle radicals include morpholino-, pyperidino-, thiomorpholino and the like.

The term "pyridyl" as used herein refers to a six membered aromatic heterocycle having one ring nitrogen atom. Examples of pyridyl are 2-pyridyl-, 3-pyridyl, 4-pyridyl.

A "pharmacological composition" refers to a mixture of one or more of the compounds described herein or pharmaceutically acceptable salts thereof, with other chemical components, such as pharmaceutically acceptable carriers and/or excipients. The purpose of a pharmacological composition is to facilitate administration of a compound to an organism.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include without limitation: ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, wool fat, sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

An "excipient" refers to an inert substance added to a pharmacological composition to further facilitate administration of a compound. Examples of excipients include but are not limited to calcium carbonate, calcium phosphate, various sugars and types of starch, cellulose derivatives, gelatine, vegetable oils and polyethylene glycols.

A "pharmaceutically effective amount" means an amount which is capable of providing a therapeutic and/or prophylactic effect. The specific dose of compound administered according to this invention to obtain therapeutic and/or prophylactic effect will, of course, be determined by the particular circumstances surrounding the case, including, for example, the specific compound administered, the route of administration, the pathophysiological conditions being treated, and the individual being treated. A typical daily dose (administered in single or divided doses) will contain a dosage level of from about 0.01 mg/kg to about 50-100 mg/kg of body weight of an active compound of the invention. Preferred daily doses generally will be from about 0.05 mg/kg to about 20 mg/kg and ideally from about 0.1 mg/kg to about 10 mg/kg. Factors such as clearance rate, half-life and maximum tolerated dose (MTD) have yet to be determined but one of ordinary skill in the art can determine these using standard procedures.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques) or via an implanted reservoir. Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

If required, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples" Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide (U.S. Pat. No. 7,014,866; and US patent publications 2006/0094744 and 2006/0079502).

Said formulation includes the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present disclosure suitable for oral administration may be presented, but not limited to, as discrete units such as capsules, sachets, tablets, drops, syrups, suspensions, emulsions, oral therapeutic systems each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, granule, fine granule, powder, couplet, pill, dry syrup, coated preparations including sugar-coated tablets, couplets, film-coated tablets and coated granulated powder, elixir, limonade, extract, drinkable preparation and soft and hard capsule agents filling liquid or semi-solid substance, multi-layer granules, multi-layer tablets or dry coated tablet, tablets by separating granules, microcapsules, foaming pharmaceutical preparation, chewable preparation, dissolving preparation in the mouth, matrix preparation, solid solutions, lozenges, suppositories, rectal solutions, etc. Soft gelatin capsules can be useful for containing such suspensions, which may beneficially increase the rate of compound absorption.

As additives for the pharmaceutical compositions of this invention, the following substances can be used without any limitations: stabilizer, surfactant, plasticizer, lubricant, solubilizer, reducing agent, buffer agent, sweetening agent, base, adsorbent, corrigent, binder, suspension, suspending agent, antioxidant, polish, coating, wetting agent, wet modifier, filler, antifoaming agent, refrigerative agent, coloring matter, flavoring agent, perfume, sugar coating agent, isotonizing agent, softener, emulsifying agent, foaming agent, pH modifier, diluent, excipient, dispersing agent, disintegrator, fragrance, desiccant, antiseptics, preservative, solubilizing agent, solubilizer, solvent, superplasticizer, antistatic agent, extender, moisturizing agent, and the like.

Examples of additives are lactose, sucrose, glucose, mannitol, sorbitol, potato starch, corn starch, wheat starch, calcium carbonate, calcium sulfate, sodium hydrogencarbonate, sodium chloride.microcrystalline cellulose, methyl cellulose, ethyl cellulose, hydroxypropyl methylcellulose, hydroxypropyl cellulose, carboxymethyl-cellulose, sodium carboxymethylcellulose, carboxy methylcellulose calcium, polyvinyl alcohol, magnesium stearate, talc, hydrogenation vegetable oil, macrogol, silicone oil, agar, calcium carbonate, sodium hydrogencarbonate, sodium alginate, shellac, glycerin, aromatic essential oil, water-soluble food dye, rake pigment, benzoic acid, sodium benzoate, para oxybenzoic acid, ester, cationic soap, dehydroacetic acid, boric acid, chlorobutanol, benzyl alcohol, polysorbate 80, fatty acid ester of glycerin, white beeswax, medium-chain triglyceride, ascorbic acid, tocopherol, sodium thiosulfate, sodium edetate, and the like. Additives that can be used for the pharmaceutical compositions of this invention are not restricted to those mentioned above, if they are available in the manufacturing pharmacy.

In the case of tablets for oral use, carriers that are commonly used include lactose, cellulose and its derivatives, sucrose, glucose, mannitol, sorbitol, xylitol, cyclodextrines, polyvinylpyrrolidone, silica, galactomannan, polyethylene glycol, polysorbates, talc, aluminium hydrosilicate, and corn starch. Lubricating agents, such as magnesium stearate, stearine, are also typically added. For oral administration in a capsule form, useful diluents include lactose and dried cornstarch. When aqueous suspensions are administered orally, the active ingredient is combined with emulsifying and suspending agents like glycerol monostearate, sorbitan stearate, polysorbates, polysaccharates, gelatins, cellulose and its derivatives, tragacanth. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration, like ready-to-use injectable solution form, epidural and intrathecal administration form, include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous solutions and suspensions for injection may be prepared from sterile powders, granules and tablets.

The solutions for injection may be in the form, for example, of a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration or in a suitable enema formulation. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered in the form of adhesive therapeutic systems These compositions can be applied on the skin by transdermal composition comprising a support and an adhesive layer laminated on one surface of the support, wherein the adhesive layer comprises an active engradient, polymers like polyisobutylene having different viscosity average molecular weights, a tackifier, and a permeation enhancer compatible with the polyisobutylene blend and the tackifier. (Prausnitz, M. R.; Langer, R.; Transdermal drug delivery. Nature Biotechnology 26: 1261-1268, 2008)

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art (See, e.g.: Rabinowitz J D and Zaffaroni A C, U.S. Pat. No. 6,803,031, assigned to Alexza Molecular Delivery Corporation).

Topical administration of the pharmaceutical compositions of this invention is especially useful when the desired treatment involves areas or organs readily accessible by topical application. For topical application topically to the skin, the pharmaceutical composition should be formulated with a suitable ointment and cream containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water.

The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

Pharmaceutical compositions comprising a compound of formula (I) as active component may additionally comprise an agent selected from the group consisting of antihistamines, calcium channel blockers, sedatives, antiepileptics, anticonvulsant, other opioid agonists and antagonists, NMDA receptor antagonist, benzodiazepines, antiaddictives, phenotiazines, antidepressants, non-steroidal anti-inflammatory drugs, local anesthetics, psychostimulants, psychedelics, anticoagulants, antitussives, glucocorticoids, muscle relaxants, parasympathomimetics, antiemetics, imidazoline receptor agonist, sympathomimetics, $\alpha_2$-adrenergic receptor agonists, GABA receptor agonists, 5-HT1A agonist, proton pump inhibitors, histamine-2 receptor antagonist, intravenous anesthetics, cannabinoids, antibiotics, inhalational anaesthetics, antihypertensives, centrally acting non-opioid analgesics, stimulants, norepinephrine reuptake inhibitors, estrogen receptor agonists, antipsychotics, TNF inhibitors, expectorants, serotonin-norepinephrine reuptake inhibitors, serotonine receptor antagonists, antitumor agents, nasal decongestants, antihistamines, vitamines antitussives or the pharmaceutical compositions comprising a compound of formula (I) may be co-administered with such agents.

The additional agents include, but are not limited to for cyclizine, naltrexone, ethorphine, paracetamol, metamizol sodium, coffein, ephedrine, naloxone, acetylsalicylic acid, ibuprofen, phenacetin, naproxen, indomethacin, diclofenac, promethazine, scopolamine, d,l-methylephedrine, chlorpheniramine, phenyltoloxamine citrate, lyzozime, romifidine, gabapentin, oxycodone, tramadol, ketamine, midazolam, mitragynine, ibogaine, pregabalin, escitalopram, citalopram, pentazocine, nalbuphine, dezocine, butorphanol, buprenorphine, ketorolac, ziconotide, cocaine, heparin, fentanyl, sufentanil, alfentanyl, remifentanil, dextromethorphan, bupivacaine, meperidine, tizanidine, alprazolam, neostigmine, norketamine, droperidol, clonidine, baclofen, lorazepam, nortriptyline, noradrenaline, carbachol, maprotiline, dexmedetomidine, omeprazole, phencyclidine, propofol, $\Delta^9$-tetrahydrocannabinol, butamben, lidocaine, nifedipine, prednisone, amitriptyline, chlordiazepoxide, cefazolin, desipramine, serotonin, hydroxyzine, clonazepam, amphetamine, alcohol, acetaminophen, dipyrone, LSD, levomepromazine, diphenhydramine, minocycline, nitrous oxide, methadone, zolpidem, ethylketazocine, lisinopril, captopril, losartan, MDMA, flupirtin, caffeine, methoxctamine, phenobarbital, amfonelic acid, nisoxetine, tamoxifen, cyclazocine, chlorpromazine, cetirizine, ranitidine, trazodone, haloperidol, bupropion, prednisone, etanercept, levobupivacaine, ropivacaine, butalbital, guaifenesin, duloxetine, ondansetron, angiostatin K1-3, DL-$\alpha$-difluoromethyl-ornithine, endostatin, fumagillin, genistein, minocycline, staurosporine, ($\pm$)-thalidomide, bleomycim, carboplatin, carmustine, chlorambucil, cyclophosphamide, cis-diamineplatinum(II) dichloride (cisplatin), melphalan, mitoxantrone, oxaliplatin ($\pm$)-amethopterin (methotrexate), 3-amino-1,2,4-benzotriazine-1,4-dioxide, aminopterin, cytosine $\beta$-D-arabinofuranoside, 5-fluoro-5'-deoxyuridine, 5-fluorouracil, ganciclovir, hydroxyurea, mitomycin C, actinomycin D, daunorubicin, doxorubicin, homoharringtonine, idarubicin, S(+)-camptothecin, curcumin, (-)-deguelin, etoposide, formestane, fostriecin, hispidin, 2-imino-1-imidazoli-dineacetic acid (cyclocreatine), mevinolin, trichostatin A, tyrphostin AG 34, tyrphostin AG 879, 5-aza-2'-deoxycytidine, 5-azacytidine, cholecalciferol (Vitamin D3), hydroxytamoxifen, melatonin, mifepristone, raloxifene, all trans-retinal (Vitamin A aldehyde), retinoic acid, all trans (Vitamin A acid), 9-cis-retinoic Acid, 13-cis-retinoic acid, retinol (Vitamin A), tamoxifen, troglitazone, colchicine, dolastatin 15, nocodazole, paclitaxel, podophyllotoxin, rhizoxin, vinblastine, vincristine, vindesine, vinorelbine (Navelbine), 17-(allylamino)-17-demethoxygeldanamycin, 4-amino-1,8-naphthalimide, apigenin, brefeldin A, cimetidine, dichloromethylene-diphosphonic acid, leuprolide (Leuprorelin), luteinizing hormone-releasing hormone, pifithrin-$\alpha$, rapamycin, sex hormone-binding globulin, thapsigargin, urinary trypsin inhibitor fragment (Bikunin), levo-methamphetamine, naphazoline, oxymetazoline, phenylephrine, phenylpropanolamine, propylhexedrine, synephrine, tetrahydrozoline, xylometazoline azelastine, hydroxyzine, desloratadine, cyproheptadine, emadastine, levocabastine, azelastine, carbinoxamine, levocetirizine, fexofenadine, diphenhydramine, brompheniramine, loratadine, clemastine, certirizine, Vitamin A (retinol), Vitamin B1 (thiamine), Vitamin B2 (riboflavin), Vitamin B3 (niacin), Vitamin B5 (pantothenic acid), Vitamin B6 (pyridoxine), Vitamin B7 (biotin), Vitamin B9 (folate), Vitamin B12 (cobalamin), Vitamin C (ascorbic acid), Vitamin D (calciferol), Vitamin E, Vitamin K, alloclamide, chloperastine, tipepidine, sodium dibunate, tipepidine, cloperastine fendizoate, codeine, dihydrocodeine, pentoxyverine, noscapine, carbetapentane, dimemorfan, benproperine, isoaminile, oxeladin, eprazinone, clobutinol, clofedanol, fominoben, I-methylephedrine, trimetoquinol, pseudoephedrine, phenylpropanolamine, methoxyphenamine, ambroxol, bromhexine, isopropamide and salts thereof.

These compositions can be prepared by methods known per se in the preparation of pharmaceutical compositions, by mixing the active material and the corresponding carriers and/or excipients. The compositions generally contain 0.1% to 95% by weight active compound.

EXAMPLES

The following examples are only for the purposes of illustration of the invention and are not intended to limit the spirit or the scope of the claims.

Preparation of the Compounds of the Invention

The compounds of formula (I) may be synthesized using conventional techniques (Przybyl, A. K.; Flippen-Anderson, J. L.; Jacobson, A. E.; Rice, K. C. J. Org. Chem. 68, 2010-2013, 2003) as described for the preparation of hydrogenated compounds but using any source of deuterium for obtaining the deuterated derivatives. Other methods like reduction with deuterides (F. A. Hochstein, Weldon G. Brownb J. Am. Chem. Soc., 70, 3484-3486, 1948) or transfer deuteration (T. Sakamoto, K. Mori, T. Akiyama Org Lett. 14, 3312-3315, 2012) may be also applied.

For example compounds of the invention may be prepared using the processes described herein. As can be appreciated by the skilled practitioner, these processes are not the only means by which the compounds described and claimed may be synthesized. Further methods will be evident to those of ordinary skill in the art.

Advantageously, the compounds of the invention are conveniently synthesized from commercially available starting materials i.e. from the corresponding 7,8-didehydro-compounds or from the derivatives thereof. The preparation of non-commercial starting compounds or intermediates is referenced herein. The deuteration of the morphine skeleton may be performed prior to the formation of O- and/or N-substituted side chains and after the deuteration the corresponding deuterated O- and/or N-substituted compounds may be obtained by known methods.

Similarly some derivatives bearing a side chain sensible to the deuteration process may be prepared from the corresponding deuterated parent compounds or also well-known protecting groups may be used for preventing the undesired reactions of a side chain during the deuteration (U.S. Pat. No. 3,254,088)

Compounds of the invention are characterized by $^1$HNMR data (recorded in deuterated solvents on a 400 MHz Bruker spectrometer) and/or mass spectra, the stereochemistry of the deuterium incorporation have been determined by the integration of the NOE cross-peaks.

General Procedures

Procedure 1

0.5 mmol dried starting material in base form has been dissolved in 150 ml ethyl acetate. The solution has been sonicated for 20 min. The deuteration reaction has been performed in an H-Cube® continuous flow reactor. The deuterium gas has been produced by the electrolysis of heavy water. The reaction parameters are as follows: 50 bar pressure, flow rate: 1 mL/min, 30° C., 5% Pd/BaSO$_4$ as catalyst. After completion of the reaction, the ethyl acetate has been evaporated and the crystalline solid or colourless oily product isolated.

Procedure 2

The product obtained in Procedure 1 wherein $R_1$, $R_2$ and/or X is OH, may be alkylated and/or acylated according to U.S. Pat. No. 3,254,088 or by any methods well known in the art.

The structure determination has been performed by using one and two dimensional NMR and mass spectra. The deuterium incorporation ratio has been determined by the application of 1H NMR and mass spectra.

The deuterium incorporation value was always higher than 95%. The acceptable values should be higher than >90%.

TABLE 1

Examplary compounds of formula (I)

| Ex. No. | $R_1$ | $R_2$ | $R_3$* | X | Dotted line | $R_6$ | Preparation/ Intermediate** |
|---|---|---|---|---|---|---|---|
| 1 | —OH | —OH | —CH$_3$ | H | absent | H | Proc. 1 |
| 2 | —OCH$_3$ | —OH | —CH$_3$ | H | absent | H | Proc. 1 |
| 3 | —O—CH$_2$—CH$_3$ | —OH | —CH$_3$ | H | absent | H | Proc. 1 |
| 4 | —O—C(=O)—CH$_3$ | —O—C(=O)—CH$_3$ | —CH$_3$ | H | absent | H | Proc. 1 |
| 5 | —OCH$_3$ | =O | —CH$_3$ | —OH | bond | H | Proc. 1 |
| 6 | —O—Ph(2,4-diNO$_2$) | —OH | —CH$_3$ | H | absent | H | Proc. 1 or 2 |
| 7 | —OH | —OH | —C$_2$H$_5$—Ph | H | absent | H | Proc. 1 or 2 |
| 8 | —O—C(=O)—CH$_3$ | —O—C(=O)—CH$_2$CH$_3$ | —CH$_3$ | H | absent | H | Proc. 1 or 2 |
| 9 | —O—C(=O)—Ph | —O—C(=O)—Ph | —CH$_3$ | H | absent | H | Proc. 1 or 2 |
| 10 | —O—C(=O)—CH$_2$CH$_3$ | —O—C(=O)—CH$_2$CH$_3$ | —CH$_3$ | H | absent | H | Proc. 1 or 2 |
| 11 | —O—C(=O)—3Py | —O—C(=O)—3Py | —CH$_3$ | H | absent | H | Proc. 1 or 2 |
| 12 | —OCH$_3$ | —O—C(=O)—CH$_3$ | —CH$_3$ | H | absent | H | Proc. 1 or 2 |
| 13 | —O—CH$_2$—Ph | —OH | —CH$_3$ | H | absent | H | Proc. 1 or 2 |
| 14 | —OH | —OCH$_3$ | —CH$_3$ | H | absent | H | Proc. 1 or 2 |
| 15 | —O—C$_2$H$_4$-morpholino | —OH | —CH$_3$ | H | absent | H | Proc. 1 or 2 |
| 16 | —O—CH$_2$—Ph | —O—C(=O)—C$_{13}$H$_{27}$ | —CH$_3$ | H | absent | H | Proc. 1 or 2 |
| 17 | —OCH$_3$ | =O | —CH$_3$ | —O-cinnamoyl | bond | H | Proc. 1 or 2 |
| 18 | —OCH$_3$ | =O | —CH$_3$ | H | bond | H | Proc. 1 or 2 |
| 19 | —OH | =O | —CH$_3$ | H | bond | H | Proc. 1 or 2 |
| 20 | —OH | =O | —CH$_3$ | —NH—C$_5$H$_{11}$ | bond | H | Proc. 1 or 2 |
| 21 | —OH | —Cl | —CH$_3$ | H | absent | H | Proc. 1 or 2 |
| 22 | —OCH$_3$ | —O—C(=O)—3Py | —CH$_3$ | H | absent | H | Proc. 1 or 2 |
| 23 | —OH | —OH | —CH$_2$—CH=CH$_2$ | H | absent | H | Proc. 1 or 2 |
| 24 | —OH | =CH$_2$ | —CH$_3$ | H | bond | H | A |
| 25 | —OH | —N(C$_2$H$_4$Cl)$_2$ | —CH$_2$—cPr | —OH | absent | H | B |
| 26 | —OH | —OH | —CH$_3$ | —OH | absent | H | C |
| 27 | —O—C(=O)—CH$_3$ | =O | —CH$_3$ | H | bond | H | D |
| 28 | —OCH$_3$ | —N—OCH$_2$—C(=O)OH | —CH$_3$ | H | bond | H | E |
| 29 | —OH | =O | —CH$_3$ | —OH | bond | H | F |
| 30 | —OH | =O | —C$_2$H$_4$O—CH$_3$ | —OH | bond | H | G |
| 31 | —OCH$_3$ | =O | —CH$_3$ | H | bond | H | F |

TABLE 1-continued

Examplary compounds of formula (I)

| Ex. No. | R₁ | R₂ | R₃* | X | Dotted line | R₆ | Preparation/ Intermediate** |
|---|---|---|---|---|---|---|---|
| 32 | —OH | —O | —CH₃ | H | bond | H | F |
| 33 | —OCH₃ | —OH | —CH₃ | —OH | absent | H | F |
| 34 | —OCH₃ | —O—C(=O)—CH₃ | —CH₃ | H | absent | H | H |
| 35 | —OH | —OH | —CH₂—cBu | —OH | absent | H | F |
| 36 | —OH | —NNH₂ | —CH₃ | —OH | bond | H | I |
| 37 | —OH | —O | R₃: —CH₂—cPr R₅: —CH₃ | —OH | bond | H | J |
| 38 | —OH | —N(CH3)—C(=O)CH=CH-3furyl | —CH₂—cPr | —OH | absent | H | K |
| 39 | —OH | —CH₂ | —CH₂—cPr | —OH | bond | H | L |
| 40 | —OH | —NNH₂ | —CH₂—CH=CH₂ | —OH | bond | H | I |
| 41 | —OH | —O | —CH₂—CH=CH₂ | —OH | bond | H | M |
| 42 | —OH | —O | —CH₂—cPr | —OH | bond | H | N |
| 43 | —OH | —O | —CH₃ | —H | bond | —CH₃ | O |
| 44 | —OH | —O | —CH₃ | —OMe | bond | —CH₃ | P |
| 45 | —OH | —O | —CH₃ | —OEt | bond | —CH₃ | Q |
| 46 | —OH | —O | —CH₃ | —O—(CH₂)₃—Ph | bond | —CH₃ | R |
| 47 | —OH | —O | —(CH₂)₂—Ph | —OEt | bond | —CH₃ | S |
| 48 | —OH | —H | —CH₃ | —H | absent | H | T |
| 49 | —OH | —OH | —H | —H | absent | H | V |
| 50 | —O—CH₃ | —OH | —H | —H | absent | H | V |
| 51 | —OH | —OH | R₃: —O R₅: —CH₃ | —H | absent | H | W |

*R₅ is absent unless it is specified otherwise
**References of Procedures/Intermediates: A: M. Adawi Abdel-Rahman, Henry W. Elliott, Robert Binks, Werner Kung, Henry Rapoport, J. Med. Chem.; 9 (1), pp 1-6 (1966) B: Portoghese PS, Larson DL, Jiang JB, Caruso TP, Takemori AE Journal of Medicinal Chemistry; [22(2): 168-173 (1979)] C: Weiss, U.; Daum, S. J. *Journal of Medical Chemistry*; 8: 123-125. (1965) D: US 20110015398 A1 E: U.S. Pat. No. 3,153,042 F: Gaik B. Kok and Peter J. Scammells; RSC Adv., 2, 11318-11325 (2012) G: Behne M, Bremerich D, Heinrich J, Schumacher H, Scherer M.: *European Journal of Clinical Pharmacology*; 46(4): 301-4 (1994) H: v. Braun Chemische Berichte; vol. 47, p. 2319 (1914) I: E. Varga, G. Toth, S. Benyhe, S. Hosztafi, A. Borsodi: Life Sciences; 40, 1579 (1987) J: Helmut Schmidhammer, Karin Mayer-Valkanover, Michaela Walla-Kugle: Helv. Chim. Acta; 73, 1986 (1990) K: Kevin K.-C. Liu, Subas M. Sakya, Christopher J. O'Donnell, Andrew C. Flick, Jin Li: Bioorg. Med. Chem.; 19, 1136 (2011) L: U.S. Pat. No. 3,814,768 M: U.S. Pat. No. 3,254,088 N: U.S. Pat. No. 3,332,950 O: U.S. Pat. No. 2,178,010 P: U.S. Pat. No. 5,886,001 Q: U.S. Pat. No. 6,476,044 R: Schutz, J; Spetea, M; Koch, M; Aceto, M D; Harris, L S; Coop, A; Schmidhammer, H: J. Med. Chem; 46, 4182 (2003) S: Lattanzi, R; Spetea, M; Schullner, F; Rief, SB; Krassnig, R; Negri, L; Schmidhammer, H: J. Med. Chem; 48, 3372 (2005) T: U.S. Pat. No. 1,980,972 V: AU/2002/329634/B2 W: Andrew C. Allen, James M. Moore, Donald A. Cooper J. Org. Chem.; 48, 3951 (1983)

1H-NMR and MS data of the compounds:

Example 1

(5α,6α,7β,8β)-3,6-dihydroxy-4,5-epoxy-17-methyl-(7,8-²H₂)-morphinan

1H-NMR (400.1 MHz, CD₃OD) δ$_H$: 6.66 (d, J=8.6 Hz, 1H, H2), 6.57 (d, J=8.6 Hz, 1H, H1), 4.58 (d, J=5.0 Hz, 1H, H5), 3.94-4.01 (m, 1H, H6), 3.38-3.47 (m, 1H, H9), 3.00-3.14 (m, 1H, H10), 2.76-2.89 (m, 1H, H16), 2.47-2.73 (m, 5H, H10, N—CH₃, H16), 2.30 (d, J=11.2 Hz, 1H, H14), 1.95-2.06 (m, 1H, H15), 1.68-1.79 (m, 1H, H15), 1.37-1.47 (m, 1H, H7), 1.03-1.13 (m, 1H, H8).

13C-NMR (100.6 MHz, CD₃OD) δ$_C$: 147.5 (C4), 139.9 (C3), 130.5 (C12), 125.0 (C11), 120.2 (C1), 118.8 (C2), 91.2 (C5), 68.0 (C6), 62.1 (C9), 48.1 (C16), 42.8 (C13), 42.4 (N—CH₃), 39.1 (C14), 36.9 (C15), 26.6 (t, J=18.7 Hz, C7), 21.9 (C10), 20.0 (t, J=18.7 Hz, C8).

MS m/z: 290.1 (M+H)⁺

Example 2

(5α,6α,7β,8β)-4,5-epoxy-6-hydroxy-3-methoxy-17-methyl-(7,8-²H₂)-morphinan

1H-NMR (400.1 MHz, CDCl₃) δ$_H$: 6.72 (d, J=8.6 Hz, 1H, H2), 6.63 (d, J=8.6 Hz, 1H, H1), 4.60 (d, J=5.0 Hz, 1H, H5), 3.98-4.07 (m, 1H, H6), 3.87 (s, 3H O—CH₃), 3.07-3.14 (m, 1H, H9), 2.93-3.06 (m, 1H, H10), 2.48-2.59 (m, 11-1, H16), 2.34-2.45 (m, 4H, H10, N—CH₃), 2.19-2.30 (in, 2H, H14, H16), 1.85-1.97 (m, 1H, H15), 1.66-1.74 (m, 1H, H15), 1.48-1.57 (m, 1H, H7) 1.05-1.16 (m, 1H, H8).

13C-NMR (100.6 MHz, CDCl₃) δ$_C$: 146.2 (C4), 141.6 (C3), 130.3 (C12), 126.8 (C11), 119.2 (C1), 113.4 (C2), 90.4 (C5), 67.1 (C6), 59.8 (C9), 56.4 (O—CH₃) 46.8 (C16), 42.9 (N—CH₃), 42.1 (C13), 40.4 (C14), 37.3 (C15), 26.7 (t, J=18.7 Hz, C7), 20.1 (C10), 18.6 (t, J=18.7 Hz, C8).

MS m/z: 304.1 (M+H)⁺

Example 3

(5α,6α,7β,8β)-4,5-epoxy-3-ethoxy-6-hydroxy-17-methyl-(7,8-²H₂)-morphinan

1H-NMR (400.1 MHz, CDCl₃) δ$_H$: 6.72 (d, J=8.6 Hz, 1H, 112), 6.61 (d, J=8.6 Hz, 1H, H1), 4.60 (d, J=5.0 Hz, 1H, 1-15), 4.06-4.17 (m, 2H, O—CH₂—CH₃), 3.99-4.06 (m, 1H, H6), 3.09-3.18 (m, 1H, H9), 2.94-3.05 (m, 1H, H10), 2.53-2.62 (m, 1H, H16), 2.37-2.50 (m, 4H, H10, N—CH₃), 2.22-2.34 (m, 2H, H14, H16), 1.86-1.99 (m, 1H, H15), 1.65-1.75 (m, 1H, H15), 1.50-1.58 (m, 1H, H7), 1.41 (t, J=8.6 Hz, 3H, O—CH₂—CH₃), 1.05-1.16 (m, 1H, H8).

13C-NMR (100.6 MHz, CDCl₃) δ$_C$: 146.4 (C4), 140.8 (C3), 130.1 (C12), 126.4 (C11), 119.1 (C1), 114.9 (C2), 90.1 (C5), 66.9 (C6), 64.8 (O—CH₂—CH₃), 59.9 (C9), 46.8 (C16), 42.7 (N—CH₃), 41.9 (C13), 40.1 (C14), 37.0 (C15), 26.6 (t, J=18.7 Hz, C7), 20.1 (C10), 18.5 (t, J=18.7 Hz, C8), 15.0 (O—CH₂—CH₃).

MS m/z: 318.1 (M+H)⁺

Example 4

(5α,6α,7β,8β)-3,6-diacetoxy-4,5-epoxy-17-methyl-(7,8-²H₂)-morphinan

1H-NMR (400.1 MHz, CDCl₃) δ$_H$: 6.83 (d, J=8.6 Hz, 1H, H2), 6.67 (d, J=8.6 Hz, 1H, H1), 5.24-5.32 (m, 1H, H6), 4.68

(d, J=5.0 Hz, 1H, H5), 3.16-3.28 (m, 11-1, H9), 2.99-3.10 (m, 1H, H10), 2.56-2.67 (m, 1H, H16), 2.42-2.55 (m, 4H, H10, N—CH$_3$), 2.29-2.40 (m, 2H, H14, H16), 2.28 (s, 3H, 3O—CO—CH$_3$), 1.86-2.01 (m, 1H, H15), 1.82 (s, 3H, 6O—CO—CH$_3$), 1.70-1.79 (m, 1H, H15), 1.60-1.69 (m, 1H, H7), 1.04-1.17 (m, 1H, H8).

13C-NMR (100.6 MHz, CDCl$_3$) δ$_C$: 170.0 (6O—CO—CH$_3$), 168.3 (3O—CO—CH$_3$), 149.4 (C3), 132.1 (C4), 131.0 (C11), 130.1 (C12), 121.9 (C2), 118.9 (C1), 87.9 (C5), 67.7 (C6), 59.7 (C9), 46.9 (C16), 42.5 (N—CH$_3$), 42.0 (C13), 40.6 (C14), 36.0 (C15), 25.1 (t, J=18.7 Hz, C7), 20.7 (C10), 20.6 (6O—CO—CH$_3$), 20.5 (3O—CO—CH$_3$), 18.4 (t, J=18.7 Hz, C8).

MS m/z: 374.1 (M+H)$^+$

Example 5

(5α,7β,8β,14β)-4,5-epoxy-14-hydroxy-3-methoxy-17-methyl-(7,8-$^2$H$_2$)-morphinan-6-one 1H-NMR (400.1 MHz, CDCl$_3$) δ$_H$: 6.72 (d, J=8.6 Hz, 1H, H2), 6.67 (d, J=8.6 Hz, 1H, H1), 5.09 (s, 1H, OH), 4.68 (s, 1H, H5), 3.91 (s, 3H, OMe), 3.14-3.25 (m, 1H, H9), 2.99-3.10 (m, 1H, H10), 2.86-2.93 (m, 1H, H10), 2.56-2.67 (m, 1H, H16), 2.40-2.53 (m, 5H, H7, H16, N—CH$_3$), 2.14-2.23 (m, 1H, H15), 1.87-2.01 (m, 1H, H15), 1.61-1.71 (m, 1H, H8).

13C-NMR (100.6 MHz, CDCl$_3$) δ$_C$: 208.8 (C6), 145.5 (C4), 143.3 (C3), 130.0 (C12), 125.4 (C11), 119.9 (C1), 115.3 (C2), 90.9 (C5), 70.7 (C17), 65.2 (C9), 57.3 (C13), 50.5 (O—CH$_3$), 45.6 (C16), 43.2 (N—CH$_3$), 36.4 (C10), 31.7 (t, J=18.7 Hz, C7), 30.8 (t, J=18.7 Hz, C8) 22.4 (C15).

MS m/z: 318.1 (M+H)$^+$

Biological Examples

Example 52

Receptor Binding Assay

The affinity for μ- and δ-opioid receptors of the compounds was tested in an in vitro receptor binding assay.

Chemicals and Radioligands

[$^3$H]DAMGO ([D-Ala$^2$,NMe-Phe$^4$,Gly$^5$-ol]enkephalin; 41 Ci/mmol) and [$^3$H]Ile$^{5,6}$-deltorphin-2 (Tyr$^1$,Ile$^{5,6}$deltorphin-2; 48 Ci/mmol) were radiolabeled in the Isotope Laboratory of BRC (Radiolab), Szeged, HungaryAll other chemicals used in this study were purchased from Sigma Chemical Co. (St. Louis, Mo., USA).

Opioid Peptides

Ile$^{5,6}$-deltorphin-2 (Tyr-D-Ala-Phe-Glu-Ile-Ile-Gly-NH$_2$) was synthesized in the Isotope Laboratory of BRC (Radiolab), Szeged, Hungaryby solid phase peptide synthesis procedure (SPPS) using the BOC chemistry method. DAMGO (H-Tyr-D-Ala-Gly-N-Me-Phe-glycinol) was purchased from Bachem.

Animals

Inbred Wistar rats (250-300 g body weight) were housed in the local animal house of the Biological Research Center (BRC, Szeged, Hungary). Animals were kept in groups of four, allowed free access to standard food and tap water and maintained on a 12:12-h light/dark cycle until the time of sacrifice. Animals were handled according to the European Communities Council Directives (86/609/ECC) and the Hungarian Act for the Protection of Animals in Research (XXVIII.tv. 32.§). Accordingly, the number of animals and their suffering were minimized.

Rat Brain Membrane Preparations

A crude membrane fraction was prepared from Wistar rat brains and spinal cords according to a method of Pasternak with small modifications (Benyhe, S.; Farkas, J.; Tóth, G.; Wollemann, M.; J. Neurosci. Res.; 48, 249 1997). Two- to three-months old animals were decapitated, and the brains without cerebella were rapidly removed, and washed several times with chilled 50 mM Tris-HCl buffer (pH 7.4). The brains were then weighed and suspended in 5 vol/wt of spinal cord tissue of the ice-cold buffer. Tissues were homogenized using a Braun teflon-glass rota-homogenizer at 4° C. (1000 revolutions per minute, 10-15 strokes), and filtered through four layers of gauze to remove large aggregates. Additional buffer was added to reach a final buffer volume/membrane pellet ratio of 30 vol/wt. After centrifugation with a Sorvall RC5C centrifuge (40,000×g, at 4° C., for 20 min), the resulting pellet was resuspended in fresh buffer (30 vol/wt) by using a vortex. The suspension was incubated at 37° C. for 30 min to remove any endogenous opioids. Centrifugation was repeated under the same conditions as described above, and the final pellet was resuspended in five volumes of 50 mM Tris-HCl buffer (pH 7.4) containing 0.32M sucrose to give a final protein concentration of 3-4 mg/mL. The membrane samples were stored in 5 ml aliquots at 70° C. The protein concentration was determined by the Bradford method. Before use the membranes were thawed and resuspended in 50 mM Tris-HCl buffer (pH 7.4) and centrifuged (40,000×g, at 4° C., for 20 min) to remove sucrose and used immediately in binding assays.

Receptor Binding Assays

All binding assays were performed at 35° C. for 45 mM in 50 mM Tris-HCl buffer (pH 7.4) in a final volume of 1 ml, containing 0.2-0.4 mg/ml membrane protein. Samples were made in disposable plastic assay tubes (Sarstedt Co., Nümbrecht, Germany) when [$^3$H]Ile$^{5,6}$deltorphin-2 was used, and glass tubes were used in the case of [$^3$H]DAMGO. Rat brain membranes were incubated with the type-specific radioprobes, such as the selective mu opioid receptor agonist [$^3$H]DAMGO (0.3-0.8 nM) or the delta opioid receptor selective agonist [$^3$H]Tyr$^1$,Ile$^{5,6}$deltorphin-2 (Tyr-n-Ala-Phe-Glu-Ile-Ile-Gly-NH$_2$; 1.5-1.9 nM) in the presence of unlabeled test ligands (their concentrations ranged from 10$^{-5}$ to 10$^{-11}$ M). Non-specific binding was determined in the presence of 10 μM DAMGO or 10 μM Ile$^{5,6}$-deltorphin-2. Reaction was terminated and bound and free radioligands were separated by rapid filtration under vacuum through Whatman GF/C (radiolabeled peptides) glass fiber filters by using Brandel M24R Cell Harvester. Filters were washed three times with 5 ml ice-cold 50 mM Tris-HCl (pH 7.4) buffer. After filtration and separation procedure had been completed, fiber-disks were dried under an infrared lamp, and then removed from the filter-sheet by tweezers. Each disk was inserted into UltimaGold™ environment friendly, non-volatile, toluene-free scintillation cocktail, then rapidly removed and placed into individual counting vials (transparent glass, Packard). Bound radioactivity was determined in Packard Tricarb 2300TR liquid scintillation analyzer. Receptor binding experiments were performed in duplicate and repeated at least three times.

Data Analysis

Radioligand binding experiments were performed in duplicate and repeated at least three times. Experimental data were analyzed and graphically processed by GraphPad Prism (version 4.00 for Windows, GraphPad Software, San Diego, Calif., USA, www.graphpad.com) research software package with standard office computers. Displacement curves were fitted by nonlinear regression using the one-site competition fitting option with no ligand depletion. The equilibrium inhibition constant ($K_i$ value) was calculated from the $IC_{50}$ values according to the built-in Cheng-Prusoff equation module ($K_i=IC_{50}/(1+([L]/K_d)$ where [L] is the concentration of free radioligand used in the assay and $K_d$ is the dissociation constant of the radioligand for the receptor.

TABLE 2

Results of receptor binding assays for the deuterated and hydrogenated samples

| Compound | $K_i^\mu$ (nM) | $K_i^\delta$ (nM) | $K_i^\delta/K_i^\mu$ |
|---|---|---|---|
| Morphine | 3.0 ± 0.09 | 586.7 ± 191.2 | 195 |
| DAMGO | 1.0 ± 0.2 | | |
| Ile$^{5'6}$-deltorphin-2 | | 0.96 ± 0.01 | |
| Ex 1 | 0.53 ± 0.08 | 69 ± 7 | 130 |
| Dihydromorphine | 1.00 ± 0.09 | 294 ± 54 | 294 |
| Ex 2 | 34.1 ± 1.08 | >10000 | |
| Dihydrocodeine | 122 ± 15 | >10000 | |
| Ex 3 | 204.6 ± 63.1 | 6122.1 ± 845.2 | 30 |
| Ex 4 | 2.89 ± 0.7 | 210.6 ± 24 | 73 |
| Ex 5 | 6.2 ± 0.7 | 871 ± 47 | 140 |
| Oxycodone | 16.4 ± 2.7 | 1446 ± 259 | 88 |

According to the results depicted in Table 2 we can say, that the deuterated compounds 1, 2 and 5 show higher affinity to μ-opioid receptors than the corresponding hydrogenated derivatives, furthermore compound 1 and 4 show higher affinity to μ-opioid receptors than the morphine. Most importantly $d_2$-dihydromorphine (1) is more active than the prototypic opioid ligand DAMGO. Moreover, the deuterated derivatives can be used as highly active pain killers in iontophoretic applications.

None of the compounds tested had affinity to delta opioid receptors, consequently they are μ-selective ligands.

Example 53

Behavioral Nociceptive Testing

The paw-withdrawal test (PWD) was used to measure the heat pain threshold after the treatments. A detailed description of this model was published by Hargreaves et al. (Hargreaves, K.; Dubner, R.; Brown, F.; Flores, C.; Joris, J. Pain; 32, 77 1988). Briefly, rats were placed on a glass surface in a plastic chamber and were allowed to acclimatize to their environment for 15-30 min before testing. The baseline hind paw-withdrawal latencies (baseline values at 0 min determined two times) were then obtained. A heat stimulus was directed onto the plantar surface of each hind paw and the intensity of the thermal stimulus was adjusted to derive an average baseline latency of approximately 10 s (cut-off time 20 s). Then the animals were treated subcutaneously with different doses of ligands (0.3-10 mg/kg). The nociceptive threshold was determined at 15-min intervals for 120 min.

Statistical Analyses

Data are presented as means±SEM. The mean of the two sides and the mean of two time points (15-30; 45-60; 75-90 and 105-102) were evaluated. The results were analyzed using a two-way ANOVA (ANalysis Of VAriances) (factors: treatment and time with repeated measurements). Subsequent analysis was performed using Fisher-LSD test. A p-value less than 0.05 was considered significant. Data were analyzed using STATISTICA 7.1. software (Statsoft Inc., Tulsa, Okla.).

Results

The baseline latencies did not indicate significant difference between the groups.

All drugs produced dose-dependent antinociception. The codein and ethylmorphine derivatives (ligands 2 and 3), showed lower potency, therefore we applied 1-10 mg/kg doses, and in the case of the more potent drugs (1 and 4) 0.3-10 mg/kg was injected. As regards the doses of morphine, all four doses were investigated and the effects of ligands were compared to morphine.

TABLE 3

Time course of the antinociceptive effects (sec) of the compounds 3 mg/kg s.c.

| Compound | Treatment time (min) | | | | |
|---|---|---|---|---|---|
| | 0 | 30 | 60 | 90 | 120 |
| Morphine | 10.1 | 14.4 | 13.9 | 13.2 | 12.8 |
| Dihydromorphine | 10.2 | 13.1 | 13.9 | 14.1 | 13.3 |
| Ex. 1 | 10.1 | 14.1 | 14.9 | 14.9 | 14.1 |
| Dihydrocodeine | 10.1 | 11.1 | 10.7 | 10.5 | 10.3 |
| Ex. 2 | 9.9 | 12.1 | 11.9 | 11.7 | 11.8 |
| Dihydroethylmorphine | 10.1 | 11.3 | 10.9 | 10.2 | 9.9 |
| Ex. 3 | 10.0 | 12.2 | 11.6 | 11.4 | 11.1 |
| Dihydroheroine | 10.1 | 17.3 | 15.6 | 12.9 | 10.7 |
| Ex. 4 | 9.7 | 19.7 | 17.9 | 14.3 | 11.4 |
| Oxycodone | 9.8 | 12.2 | 12.6 | 11.9 | 10.6 |
| Ex. 5 | 9.9 | 13.3 | 13.7 | 13.6 | 12.1 |

3 mg/kg dose was effective for all ligands. ANOVA with repeated measurements showed significant effects of treatment ($F_{5,30}=23.1$, $p<0.001$), time ($F_{4,120}=26.4$, $p<0.001$), and interaction ($F_{20,120}=6.9$, $p<0.001$). As regards the comparison of the ligands to morphine, ligands 1 and were more effective than morphine. Moreover ligands 1 and 4 produced more prolonged effects compared to other drugs.

TABLE 4

Time course of the antinociceptive effects (sec) of the compounds 10 mg/kg s.c.

| Compound | Treatment time (min) | | | | |
|---|---|---|---|---|---|
| | 0 | 30 | 60 | 90 | 120 |
| Morphine | 9.9 | 18.2 | 18.8 | 14.4 | 10.5 |
| Dihydromorphine | 10.1 | 19.4 | 20.6 | 15.3 | 14.1 |
| Ex. 1 | 9.8 | 21.3 | 22.1 | 16.8 | 16.1 |
| Dihydrocodeine | 9.9 | 13.4 | 13.6 | 10.9 | 9.8 |
| Ex. 2 | 10.1 | 14.2 | 14.8 | 14.9 | 14.1 |
| Dihydroethylmorphine | 10.2 | 11.5 | 12.3 | 12.0 | 10.4 |
| Ex. 3 | 10.1 | 12.1 | 13.1 | 12.9 | 11.1 |

As regards to ligands 2 and 3, both ligands showed the same tendency in effect as the morphine derivative 1 i.e. an increased and prolonged the effect could be measured when compared to their non-deuterated analogues.

The invention claimed is:

1. A compound of general formula (I)

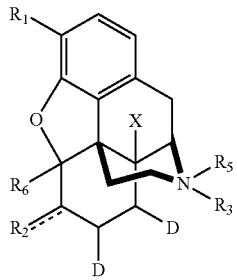

wherein
R$_1$ is —OH, —OR$_4$, —O-2,4-dinitrophenyl, —OC(=O) C$_{1-6}$ alkyl, —OC(=O)phenyl, —OC(=O)pyridyl;
R$_2$ is hydrogen, —OH, —OR$_4$, —Cl, —N$_3$, bis(2-chloroethyl)amino-, —OC(=O)—C$_{1-16}$ alkyl, —OC(=O) phenyl, —OC(=O)pyridyl, —(N-methyl-N—C (=O)—CH=CH-fur-3-yl), and the dotted line is absent or
R$_2$ is —O, —CH$_2$, —N—NH$_2$, —NOH, —N—O— C$_{1-6}$alkyl wherein the alkyl is optionally substituted with a caboxyl group, and the dotted line represents a chemical bond,
R$_3$ is hydrogen, —O, —C$_{1-6}$ alkyl optionally substituted by phenyl, (C$_{3-7}$ cycloalkyl)-(C$_{1-6}$ alkyl)-, —(C$_{1-6}$alkyl)-O—(C$_{1-6}$alkyl), —C$_{2-7}$ alkenyl;
R$_4$ is —C$_{1-6}$ alkyl optionally substituted by a phenyl or by a 6 membered saturated heterocycle attached by a nitrogen and containing at least one more heteroatom selected from O, S and N;
R$_5$ is absent or is —C$_{1-6}$ alkyl and the ring nitrogen bears a positive charge, with the proviso that R$_5$ is not absent when R$_2$ is =O;
R$_6$ is hydrogen, —C$_{1-6}$ alkyl;
X is hydrogen, —OH, —OR$_4$, —O-cinnamoyl, —NH (C$_{1-6}$ alkyl);
D is deuterium
and stereoisomers including enantiomers, diastereomers, racemic mixtures, mixtures of enantiomers or combinations thereof, as well as tautomers and salts thereof.

2. The compound of claim 1 wherein
R$_1$ is —OH, —O-methyl, —O-ethyl-, —O-benzyl, —O-(2,4-dinitro)phenyl, —O-acetyl, —O-propionyl, —O-benzoyl, —O—(C=O)nicotinyl, —O-(2-morpholino)-ethyl;
R$_2$ is —H, —OH, —Cl, bis(2-chloroethyl)amino-, —O-methyl, —O-propionyl, —O-acetyl, —O-benzoyl, —O—(C=O)nicotinyl, —O—(C=O)myristyl, —(N-methyl-N—C(=O)— —CH=CH-fur-3-yl) and the dotted line is absent, or
R$_2$ is —CH$_2$, —O, —N—O—CH$_2$COOH, —N—NH$_2$, and the dotted line represents a chemical bond;
R$_3$ is —H, —O, -methyl, cyclopropylmethyl-, phenylethyl-, -pentyl, methoxyethyl-, cyclobutylmethyl-, -allyl;
R$_4$ is —H, -methyl, -ethyl, benzyl;
R$_5$ is -methyl and the ring nitrogen bears a positive charge;
R$_6$ is —H, -methyl;
X is hydrogen, —OH, —O-cinnamoyl, —NHpentyl, —O-methyl, —O-ethyl, —O—(CH$_2$)$_3$-Ph;
D is deuterium
and stereoisomers including enantiomers, diastereomers, racemic mixtures, mixtures of enantiomers or combinations thereof, as well as tautomers and salts thereof.

3. The compound of claim 1 selected form the group consisting of
(5α,6α,7β,8β)-3,6-dihydroxy-4,5-epoxy-17-methyl-(7,8-$^2$H2)-morphinan,
(5α,6α,7β,8β)-4,5-epoxy-6-hydroxy-3-methoxy-17-methyl-(7,8-$^2$H2)-morphinan,
(5α,6α,7β,8β)-4,5-epoxy-3-ethoxy-6-hydroxy-17-methyl-(7,8-$^2$H2)-morphinan,
(5α,6α,7β,8β)-3,6-diacetoxy-4,5-epoxy-17-methyl-(7,8-2H$_2$)-morphinan
and stereoisomers, enantiomers, diastereomers, racemic mixtures, mixtures of enantiomers or combinations thereof, as well as tautomers and salts thereof.

4. A pharmaceutical composition comprising a compound of general formula (I) of claim 1 or stereoisomers including enantiomers, diastereomers, racemic mixtures, mixtures of enantiomers or combinations thereof, as well as tautomers and salts thereof and one or more pharmaceutically acceptable carriers and/or excipients.

5. A pharmaceutical comprising the compound of general formula (I) according to claim 2.

6. The pharmaceutical composition of claim 4 in the form of capsules, sachets, tablets, powders, granules, drops, syrups, suspensions, emulsions, oral therapeutic systems, soft gelatin capsules, lozenges, bolus, fine granule, powder, couplet, pill, dry syrup, coated preparations including sugar-coated tablets, couplets, film-coated tablets and coated granulated powder, elixir, limonade, extract, drinkable preparation and soft and hard capsule agents filling liquid or semi-solid substance, multi-layer granules, multi-layer tablets or dry coated tablet, tablets by separating granules, microcapsules, foaming pharmaceutical preparation, chewable preparation, dissolving preparation in the mouth, matrix preparation, solid solutions, lozenges, suppositories, rectal solutions, ready-to-use injectable solution, sterile injectable aqueous or oleaginous suspension, sterile powders, granules, tablets, suppositories, adhesive therapeutic systems, nasal aerosol or inhalation system, ointment, cream, enema formulation, iontophoretic application, coating an implantable medical device.

7. A pharmaceutical composition comprising a compound of general formula (I) of claim 1 or stereoisomers including enantiomers, diastereomers, racemic mixtures, mixtures of enantiomers or combinations thereof, as well as tautomers and salts thereof in a combination with one or more active agents.

8. The pharmaceutical composition of claim 7 wherein the one or more active agents are selected from the group consisting of antihistamines, calcium channel blockers, sedatives, antiepileptics, anticonvulsant, other opioid agonists and antagonists, NMDA receptor antagonist, benzodiazepines, antiaddictives, phenotiazines, antidepressants, non-steroidal anti-inflammatory drugs, local anesthetics, psychostimulants, psychedelics, anticoagulants, antitussives, glucocorticoids, muscle relaxants, parasympathomimetics, antiemetics, imidazoline receptor agonist, sympathomimetics, α$_2$-adrenergic receptor agonists, GABA receptor agonists, 5-HT1A agonist, proton pump inhibitors, histamine-2 receptor antagonist, intravenous anesthetics, cannabinoids, antibiotics, inhalational anaesthetics, antihypertensives, centrally acting non-opioid analgesics, stimulants, norepinephrine reuptake inhibitors, estrogen receptor agonists, antipsychotics, TNF inhibitors, expectorants, serotonin-norepinephrine reuptake inhibitors, serotonine receptor antagonists, antitumor agents, nasal decongestants, antihistamines, vitamines antitussives or the pharmaceutical compositions comprising a compound of formula (I) may be co-administered with such agents.

9. The pharmaceutical composition of claim 7 wherein the one or more additional active agents are selected from the group consisting of cyclizine, naltrexone, ethorphine, paracetamol, metamizol sodium, coffein, ephedrine, naloxone, acetylsalicylic acid, ibuprofen, phenacetin, naproxen, indomethacin, diclofenac, promethazine, scopolamine, d,l-methylephedrine, chlorpheniramine, phenyltoloxamine citrate, lyzozime, romifidine, gabapentin, oxycodone, tramadol, ketamine, midazolam, mitragynine, ibogaine, pregabalin, escitalopram, citalopram, pentazocine, nalbuphine, dezocine, butorphanol, buprenorphine, ketorolac, ziconotide, cocaine, heparin, fentanyl, sufentanil, alfentanyl, remifentanil, dextromethorphan, bupivacaine, meperidine, tizanidine, alprazolam, neostigmine, norketamine, droperidol, clonidine, baclofen, lorazepam, nortriptyline, noradrenaline, carbachol, maprotiline, dexmedetomidine, omeprazole, phencyclidine, propofol, $\Delta^9$-tetrahydrocannabinol, butamben, lidocaine, nifedipine, prednisone, amitriptyline, chlordiazepoxide, cefazolin, desipramine, serotonin, hydroxyzine, clonazepam, amphetamine, alcohol, acetaminophen, dipyrone, LSD, levomepromazine, diphenhydramine, minocycline, nitrous oxide, methadone, zolpidem, ethylketazocine, lisinopril, captopril, losartan, MDMA, flupirtin, caffeine, methoxetamine, phenobarbital, amfonelic acid, nisoxetine, tamoxifen, cyclazocine, chlorpromazine, cetirizine, ranitidine, trazodone, haloperidol, bupropion, prednisone, etanercept, levobupivacaine, ropivacaine, butalbital, guaifenesin, duloxetine, ondansetron, angiostatin K1-3, DL-α-difluoromethyl-ornithine, endostatin, fumagillin, genistein, minocycline, staurosporine, (±)-thalidomide, bleomycim, carboplatin, carmustine, chlorambucil, cyclophosphamide, cis-diammineplatinum(II) dichloride (cisplatin), melphalan, mitoxantrone, oxaliplatin (±)-amethopterin (methotrexate), 3-amino-1,2,4-benzotriazine-1,4-dioxide, aminopterin, cytosine β-D-arabinofuranoside, 5-fluoro-5'-deoxyuridine, 5-fluorouracil, ganciclovir, hydroxyurea, mitomycin C, actinomycin D, daunorubicin, doxorubicin, homoharringtonine, idarubicin, S(+)-camptothecin, curcumin, (−)-deguelin, etoposide, formestane, fostriecin, hispidin, 2-imino-1-imidazoli-dineacetic acid (cyclocreatine), mevinolin, trichostatin A, tyrphostin AG 34, tyrphostin AG 879, 5-aza-2'-deoxycytidine, 5-azacytidine, cholecalciferol (Vitamin D3), hydroxytamoxifen, melatonin, mifepristone, raloxifene, all trans-retinal (Vitamin A aldehyde), retinoic acid, all trans (Vitamin A acid), 9-cis-retinoic acid, 13-cis-retinoic acid, retinol (Vitamin A), tamoxifen, troglitazone, colchicine, dolastatin 15, nocodazole, paclitaxel, podophyllotoxin, rhizoxin, vinblastine, vincristine, vindesine, vinorelbine (Navelbine), 17-(allylamino)-17-demethoxygeldanamycin, 4-amino-1,8-naphthalimide, apigenin, brefeldin A, cimetidine, dichloromethylene-diphosphonic acid, leuprolide (Leuprorelin), luteinizing hormone-releasing hormone, pifithrin-α, rapamycin, sex hormone-binding globulin, thapsigargin, urinary trypsin inhibitor fragment (Bikunin), levo-methamphetamine, naphazoline, oxymetazoline, phenylephrine, phenylpropanolamine, propylhexedrine, synephrine, tetrahydrozoline, xylometazoline azelastine, hydroxyzine, desloratadine, cyproheptadine, emadastine, levocabastine, azelastine, carbinoxamine, levocetirizine, fexofenadine, diphenhydramine, brompheniramine, loratadine, clemastine, certirizine, Vitamin A (retinol), Vitamin B1 (thiamine), Vitamin B2 (riboflavin), Vitamin B3 (niacin), Vitamin B5 (pantothenic acid), Vitamin B6 (pyridoxine), Vitamin B7 (biotin), Vitamin B9 (folate), Vitamin B12 (cobalamin), Vitamin C (ascorbic acid), Vitamin D (calciferol), Vitamin E, Vitamin K, alloclamide, chloperastine, tipepidine, sodium dibunate, tipepidine, cloperastine fendizoate, codeine, dihydrocodeine, pentoxyverine, noscapine, carbetapentane, dimemorfan, benproperine, isoaminile, oxeladin, eprazinone, clobutinol, clofedanol, fominoben, I-methylephedrine, trimetoquinol, pseudoephedrine, phenylpropanolamine, methoxyphenamine, ambroxol, bromhexine, isopropamide and salts thereof.

10. The pharmaceutical composition according to claim 7 wherein the one or more active agents are selected from the group consisting of cyclizine, naltrexone, buprenorphine, ethorphine, paracetamol, metamizol, coffein, ephedrine, naloxone, acetylsalicylic acid, ibuprofen, phenacetin, naproxen, indomethacin, diclofenac, promethazine, scopolamine, d,l-methylephedrine, chlorpheniramine, phenyltoloxamine, lyzozime and pharmacologically acceptable salts thereof.

11. The pharmaceutical composition according to claim 7 wherein the additional active agent is administered to a patient simultaneously, separately or sequentially with a compound of the general formula (I).

12. A process for the preparation of compounds of general formula (I) of claim 1 and the salts thereof said process comprising reacting a 7,8-didehydro-morphine derivative of general formula (II)

(II)

wherein $R_1$, $R_2$, $R_3$, $R_4$, $R_5$, $R_6$ and X are defined in claim 1, with deuterium gas in the presence of a catalyst or with organic and inorganic deuteride ion or deuterium radical or deuterium gas sources and optionally transforming the compound obtained into a salt.

13. The process of claim 12 wherein the reaction proceeds in a reactor at a pressure between 2-500 bars, with deuterium gas in the presence of $Pd/BaSO_4$ catalyst at a temperature range of 20-100° C. in an aprotic solvent.

14. A method for the treatment of pain or cough, said method comprising administering to a patient in need thereof a compound of general formula (I) or stereoisomers including enantiomers, diastereomers, racemic mixtures, mixtures of enantiomers or combinations thereof, as well as tautomers and salts thereof according to claim 1.

15. The method of claim 14 wherein the compound of general formula (I) or stereoisomers including enantiomers, diastereomers, racemic mixtures, mixtures of enantiomers or combinations thereof, as well as tautomers and salts thereof is administered orally together with one or more pharmaceutically acceptable carriers and/or excipients.

16. The compound of claim 1 wherein
$R_2$ is hydrogen, —OH, —$OR_4$, —Cl, —$N_3$, bis(2-chloroethyl)amino-, —OC(=O)—$C_{1-6}$alkyl, —OC(=O)

phenyl, —OC(=O)pyridyl, —(N-methyl-N—C(=O)—CH=CH-fur-3-yl), and the dotted line is absent or R$_2$ is —CH$_2$, —N—NH$_2$, —NOH, —N—O—C$_{1-6}$alkyl wherein the alkyl is optionally substituted with a caboxyl group, and the dotted line represents a chemical bond.

17. The method of claim 14 wherein

R$_1$ is —OH, —O-methyl, —O-ethyl-, —O-benzyl, —O-(2,4-dinitro)phenyl, —O-acetyl, —O-propionyl, —O-benzoyl, —O—(C=O)nicotinyl, —O-(2-morpholino)-ethyl;

R$_2$ is —H, —OH, —Cl, bis(2-chloroethyl)amino-, —O-methyl, —O-propionyl, —O-acetyl, —O-benzoyl, —O—(C=O)nicotinyl, —O—(C=O)myristyl, —(N-methyl-N—C(=O)— —CH=CH-fur-3-yl) and the dotted line is absent, or R$_2$ is —CH$_2$, —O, —N—O—CH$_2$COOH, —N—NH$_2$, and the dotted line represents a chemical bond;

R$_3$ is —H, —O, -methyl, cyclopropylmethyl-, phenyl-ethyl-, -pentyl, methoxyethyl-, cyclobutylmethyl-, -allyl;

R$_4$ is —H, -methyl, -ethyl, benzyl;

R$_5$ is -methyl and the ring nitrogen bears a positive charge;

R$_6$ is —H, -methyl;

X is hydrogen, —OH, —O-cinnamoyl, —NHpentyl, —O-methyl, —O-ethyl, —O—(CH$_2$)$_3$-Ph;

D is deuterium.

18. The method of claim 14 wherein the compound is selected from the group consisting of (5α,6α,7β,8β)-3,6-dihydroxy-4,5-epoxy-17-methyl-(7,8-$^2$H2)-morphinan, (5α,6α,7β,8β)-4,5-epoxy-6-hydroxy-3-methoxy-17-methyl-(7,8-$^2$H2)-morphinan, (5α,6α,7β,8β)-4,5-epoxy-3-ethoxy-6-hydroxy-17-methyl-(7,8-$^2$H2)-morphinan, (5α,6α,7β,8β)-3,6-diacetoxy-4,5-epoxy-17-methyl-(7,8-$^2$H2)-morphinan and stereoisomers, enantiomers, diastereomers, racemic mixtures, mixtures of enantiomers or combinations thereof, as well as tautomers and salts thereof.

19. The method of claim 14 wherein the compound of general formula (I) or stereoisomers, enantiomers, diastereomers, racemic mixtures, mixtures of enantiomers or combinations thereof, as well as tautomers and salts thereof is in the form of a pharmaceutical composition in combination with one or more active agents.

* * * * *